United States Patent [19]

Boutonnat et al.

[11] Patent Number: 4,608,552

[45] Date of Patent: Aug. 26, 1986

[54] PROCESS AND DEVICE FOR THE REMOTE TRANSMISSION OF SIGNALS AND APPLICATION TO THE DETECTION AND/OR MEASUREMENT OF THE QUANITY OF COMBUSTIBLE GAS IN AN ATMOSPHERE

[75] Inventors: Maurice Boutonnat, Gouvieux; Gérard Rose, Villers Saint Paul, both of France

[73] Assignee: Charbonnages de France, Paris, France

[21] Appl. No.: 449,153

[22] Filed: Dec. 13, 1982

[30] Foreign Application Priority Data

Dec. 14, 1981 [FR] France ................... 81 23272

[51] Int. Cl.[4] .................. H04Q 9/00; G08C 19/16
[52] U.S. Cl. ................. 340/310 R; 340/310 A; 340/870.13
[58] Field of Search .......... 340/310 R, 310 A, 870.21, 340/870.29, 870.13; 307/3, 140

[56] References Cited

U.S. PATENT DOCUMENTS

| | | | |
|---|---|---|---|
| 3,483,546 | 12/1969 | Ausfeld | 340/310 A |
| 3,967,264 | 6/1976 | Whyte | 340/310 A |
| 4,007,458 | 2/1977 | Hollabaugh | 340/310 R |
| 4,077,030 | 2/1978 | Helava | 340/870.21 |
| 4,198,621 | 4/1980 | Roper | 340/870.39 |
| 4,222,035 | 9/1980 | Lohoff | 340/310 A |
| 4,357,606 | 11/1982 | Fortescue | 340/870.29 |
| 4,398,178 | 8/1983 | Russ | 340/310 A |
| 4,418,333 | 11/1983 | Schwarzbach | 340/310 A |
| 4,422,073 | 12/1983 | Winner | 340/870.21 |
| 4,464,653 | 8/1984 | Winner | 340/870.16 |

FOREIGN PATENT DOCUMENTS

| | | |
|---|---|---|
| 2428173 | 1/1976 | Fed. Rep. of Germany . |
| 2350461 | 12/1977 | France . |
| 2427466 | 12/1979 | France . |

Primary Examiner—John W. Caldwell, Sr.
Assistant Examiner—Michael F. Heim
Attorney, Agent, or Firm—Finnegan, Henderson, Farabow, Garrett & Dunner

[57] ABSTRACT

A process of remote transmission of signals issued by at least one sensor over a transmission line, wherein the power necessary to supply the sensor is transmitted by that line in the form of an alternating current signal of approximately constant intensity, and wherein the line fulfills the triple function of supplying power to that sensor, of transmitting interrogation signals from a central station to that sensor and of transmitting data signals in response to that interrogation signal from the sensor to the central station. A device for incorporating this process is also disclosed.

18 Claims, 11 Drawing Figures

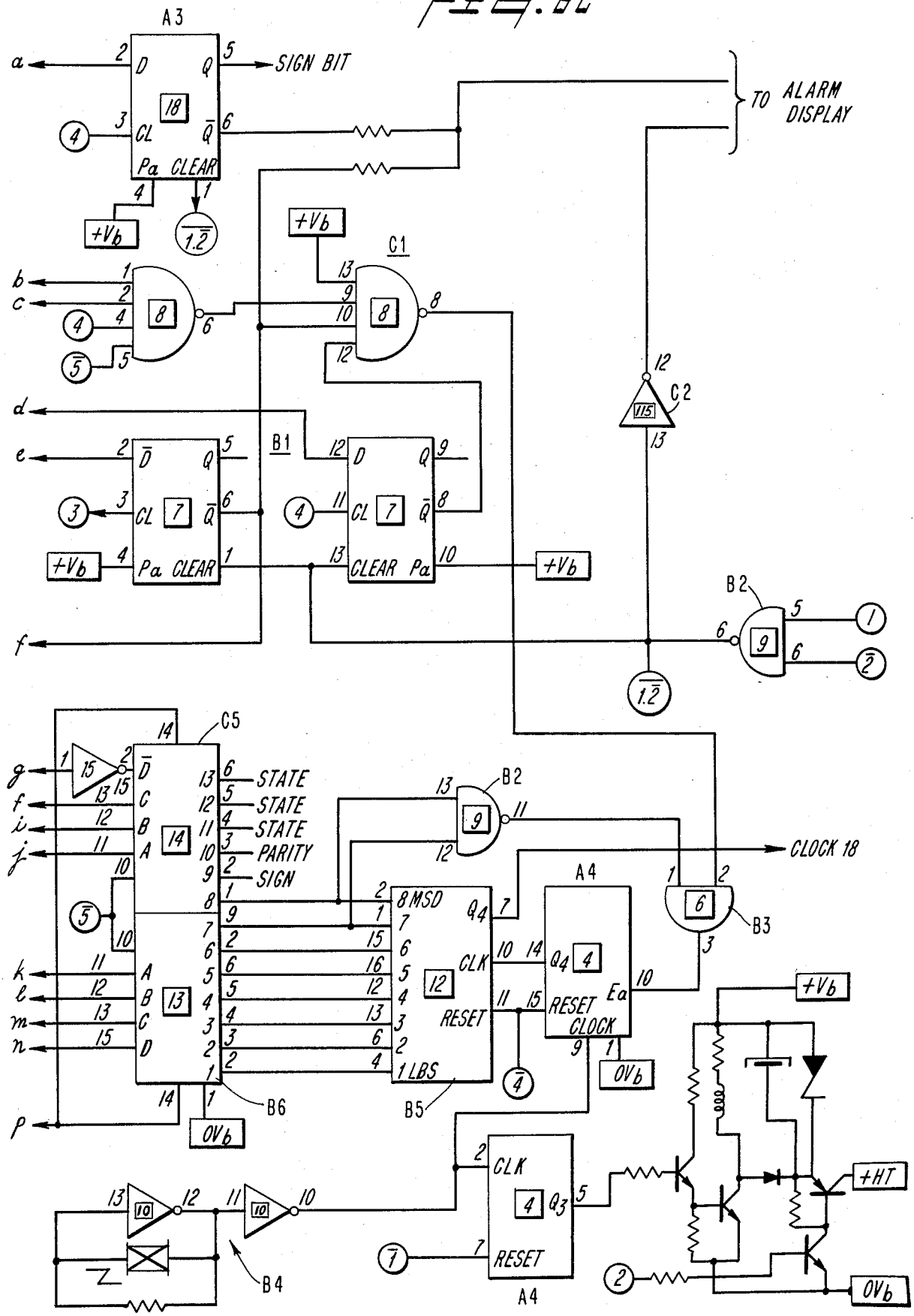

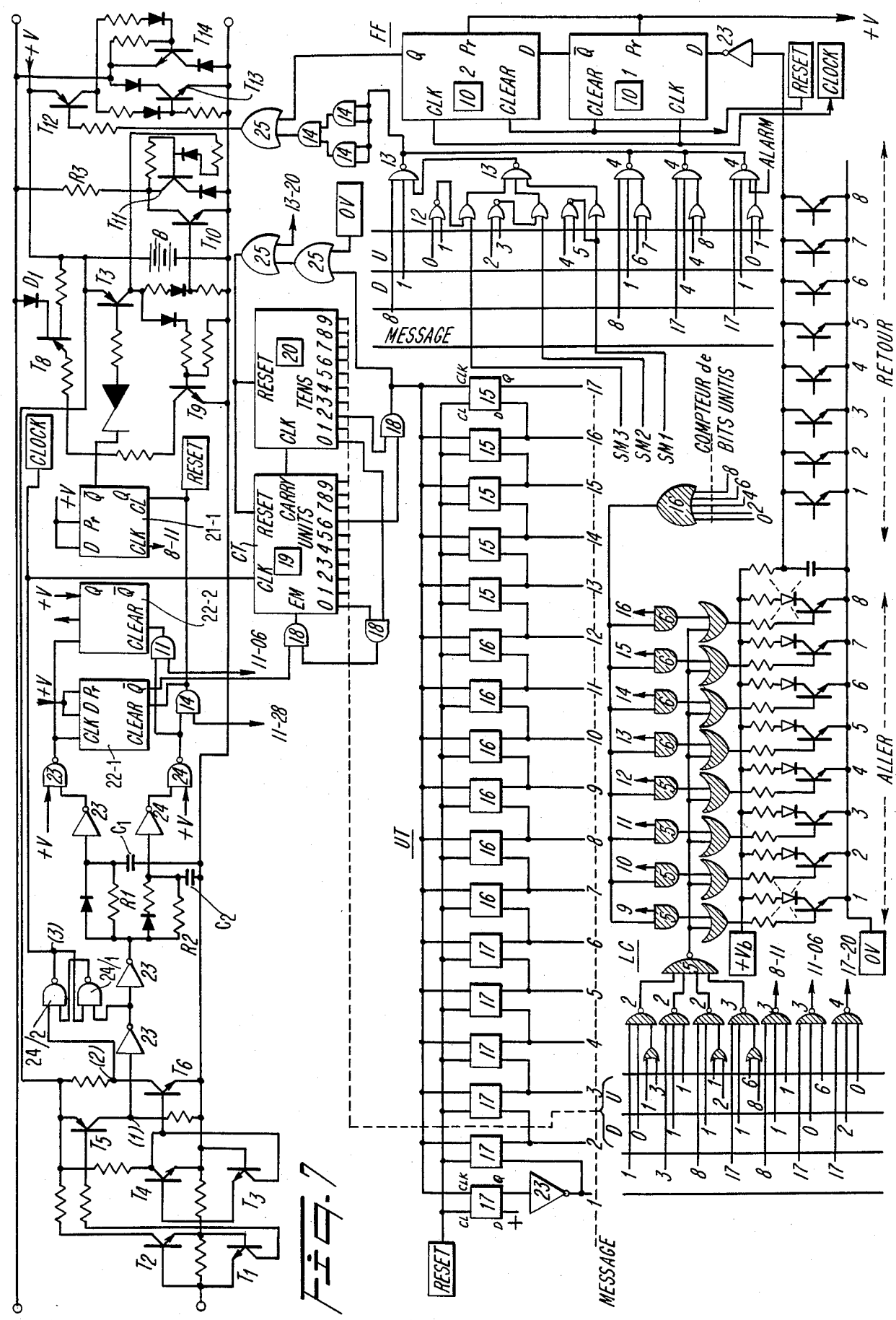

PROCESS AND DEVICE FOR THE REMOTE TRANSMISSION OF SIGNALS AND APPLICATION TO THE DETECTION AND/OR MEASUREMENT OF THE QUANITY OF COMBUSTIBLE GAS IN AN ATMOSPHERE

BACKGROUND OF THE INVENTION

I. Field of the Invention

The present invention relates to a process and a device for remote transmission of signals and the application of this process and device to the detection and/or measurement of the amount of combustible gas in an atmosphere.

II. Description of the Prior Art

Transmission of power to a remotely located sensor by means of a line which also provides both the transmission of an interrogation signal to that sensor and data signals from that sensor is known. One such process and device is described in French Pat. No. 2,350,461. The process and device described therein provides a power supply signal to a remotely located sensor by means of conveying a direct current in a line which connects that sensor to a central station, such as a central processing unit. This process and device sends an interrogation signal from the central station to the sensor in the form of a direct current signal on that line, which direct current signal is of reverse polarity to the direct current signal used to power the sensor. If it is desired to supply a multiplicity of sensors by means of a single line, such prior art processes and devices cannot supply the line with an adequate amount of direct current due to the intrinsic power consumption of the sensors and the limit on the amount of direct current which can be applied to the line in view of the safety hazards a high amount of direct current presents.

It is, accordingly, a primary object of the present invention to provide a process and device for remote transmission of signals issued by at least one sensor to a central station, which sensor is supplied by power over a remote transmission line, and wherei the power necessary to adequately supply that sens r and preferably even the power necessary to operate electronic circuits with which the sensor is associated, is transmitted by the line.

Another object of the present invention is to provide such a process and a device which fulfills the triple function of supplying power to the sensor and preferably to the circuits associated with that sensor, of transmitting interrogation signals to that sensor, and of transmitting data signals from that sensor to a central station.

Another object of the present invention is to provide such a process and device in which the transmission line can transmit interrogation signals to, and data signals from, at least one sensor which is not supplied with power from that line.

A still further object of the present invention is to make possible the powering of remotely located sensors (more particularly to ensure adequate charging of batteries which operate to power such sensors) by means of a low current intensity signal on the transmission line.

Additional objects and advantages of the invention will be set forth in part in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention as embodied and broadly described herein, a process for remotely transmitting data signals issued by at least one sensor from that sensor to a central station over a transmission line is provided which comprises the steps of: (a) supplying to the transmission line an alternating current signal of approximately constant current intensity; (b) coupling at least one sensor to that line to power that sensor using the alternating current signal on the line; (c) employing the alternating current signal to transmit an interrogation signal from the central station to the sensor over the transmission line; and (d) employing the alternating current signal to transmit a data signal from the sensor to the central station over the transmission line in response to receipt of the interrogation signal.

The process of the present invention further preferably includes the step of using the alternating current signal to power electronic circuits associated with the sensor; the step of employing the alternating current signal to transmit an interrogation signal over the transmission line from the central station to a sensor which is not powered by the alternating current signal; the step of transmitting interrogation and data signals over the transmission line in digital form; the step of transmitting a data signal wherein one complete unit of digital information is transmitted in each complete cycle of the alternating current signal; the step of transmitting an interrogation signal which includes removing the alternating current signal from the transmission line during two consecutive cycles of the alternating current signal; and the steps of generating a non-linear analog signal in response to operation of the sensor and converting that non-linear analog signal into a digital signal for transmission over the line by comparing the analog signal to a reference voltage which is a function of time and which has a representative curve comprising n straight light segments.

The process of the present invention is particularly adapted to detecting and/or measuring a quantity of combustible gas in an atmosphere using at least one sensor.

There is further provided a device for carrying out the above-summarized process.

In accordance with the process and device of the present invention it is possible to power remotely located sensors (more particularly to ensure the charging of batteries used to power such sensors) by means of a signal having a low current intensity (for example, on the order of several milliamps) owing to the presence of adequate transformers on the line. In addition, the process and device of the present invention make it possible to use an alternating current signal on a transmission line to transmit interrogation and data signals instead of utilizing a direct current signal. To achieve this advantageous result, the currents circulating in the lines and in the transformers are maintained in a constant phase relationship with respect to one another.

BRIEF DESCRIPTION OF THE DRAWINGS

The accompanying drawings, which are incorporated in and constitute a part of the specification, illustrate a preferred embodiment of the invention and, together with the general description of the invention given above, and the detailed description of the preferred embodiment given below, serve to explain the principles of the invention.

FIG. 5a illustrates the reference signal function $V = F(t)$ and FIG. 5b diagrammatically illustrates a device for converting the analog output of a sensor to a digital value using the reference signal illustrated in FIG. 5a;

FIGS. 6a, 6b and 6c show a schematic diagram of a sensor arranged for measuring the quantity of combustible gas in an atmosphere and for transmitting, upon interrogation, signals indicating that quantity to a central station in accordance with the teachings of the present invention; and FIG. 7 is a schematic diagram of a downstream modem incorporating the teachings of the present invention.

DESCRIPTION OF THE PREFERRED EMBODIMENT

Reference will now be made in detail to the present preferred embodiment of the invention as illustrated in the accompanying drawings.

In the description which follows that part of a device located close to a central station will be called "upstream" and that part of a device located close to a sensor will be called "downstream." A modulator-demodulator will be referred to as a "modem."

In accordance with the present invention at least one remotely located downstream sensor is coupled to an upstream central station by means of a transmission line. An alternating current signal of approximately constant intensity is introduced onto that line, preferably at the central station or upstream end of that line. Transformers may be employed to maintain adequate voltage in the line. Whatever the impedance and length of the transmission line, a variation in the load resistance at a transformer secondary, installed for example, upstream of the sensor, is translated into a variation in the voltage at the primary terminals of that transformer. This variation in voltage will be transmitted from the downstream end of the transmission line where the sensor is located to the upstream end of the transmission line by virtue of the currents within the line being maintained constant. Accordingly, the same value of voltage variation will be obtained at both ends of the line. These variations can be transmitted either from the downstream end to the upstream end or from the upstream end to the downstream end of the line. Accordingly, such variations can be used to provide digital transmission of an interrogation signal from the central station to the sensors or of digital signals from the sensors to the central station via the transmission line.

For example, a 0 bit can be transmitted when the resistance at the terminals of a transformer secondary associated with the sensor has a value R and a 1 bit can be transmitted when this resistance has a value R' which is different (preferably greater) than R. Measurement of the voltage at the opposite end of the line will be possible to distinguish a 1 bit from a 0 bit.

Figure 1:
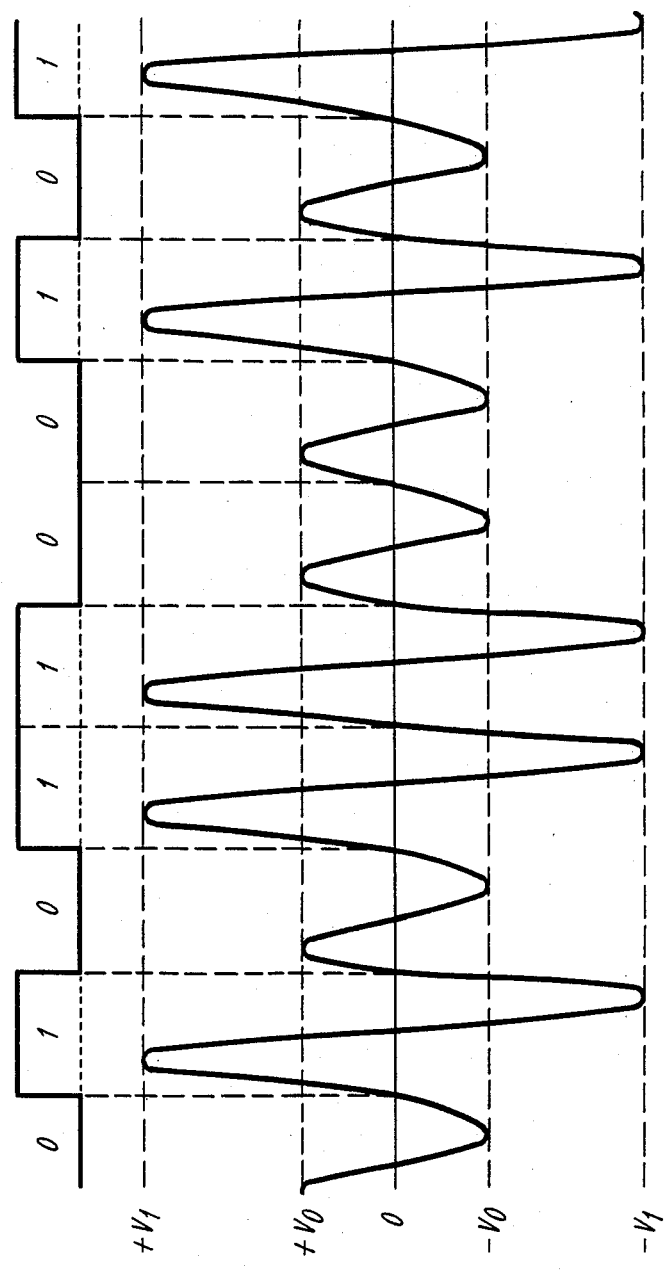
FIG. 1 illustrates data signals supplied by a sensor in accordance with the teachings of the present invention.

A message supplied by an interrogated sensor at the downstream end of the line could thus be conveyed on the line to the upstream located central station in a form shown diagrammatically by way of the example of FIG. 1.

To avoid creating interference it is necessary to switch from R to R' and vise versa when the alternating current signal passes through a null or zero voltage level. It is moreover advantageous, in order to ensure good reliability of the transmission of data from one end of the line to the other, to choose to transmit each bit of digital information in one complete period of the alternating current signal. Accordingly, each 0 bit is followed by a 1 bit and each 1 bit is followed by a 0 bit so that each unit of digital information is transmitted in one complete cycle of the alternating current signal. Synchronization between the two ends of the line is then ensured by the alternating current itself. Moreover, any batteries used to provide power to the sensor which are being charged by the alternating current signal on the line to operate the sensors or associated circuitry should be disconnected from the line during the transmission of data signals.

The process of remote transmission of data according to the subject invention can, in addition, be achieved by interrupting a selected number of consecutive periods of the alternating power supply current of the line. This mode of data transmission is particularly advantageously used to provide an interrogation signal on the line which passes from the central station to the sensors, indicating that the sensors should subsequently return data information to the central station. It is preferable that the alternating current signal on the transmission line be interrupted for two consecutive periods in order to indicate transmission of such an interrogation signal.

The process according to the present invention can be further characterized by the feature of having the digital data signals transmitted from the sensors over the line to the central station be formulated as the result of a conversion of sensor generated non-linear analog signals. This is preferred since the sensors with which the subject invention is preferably contemplated as being used emit non-linear signals which represent detected physical magnitudes. In order that the digital value X of these physical magnitudes be correctly determined, a non-linear analog signal S emitted by a detector in the sensor is compared with a reference voltage signal. This reference voltage signal varies as a function of time in a manner represented by n end-to-end connected straight line segments. This function, $V = F(t)$, can be generated with the aid of n+1 voltage operational amplifiers and has the same trend or characteristic curve as the detector's response curve $S = F(x)$.

The signals S and V are then compared. A device which comprises an electronic clock, generating pulses at a fixed rate, and a counter which counts the pulses is associated with the comparator whereby counting the number of pulses generated begins when the comparison operation is begun and stops when the reference voltage V becomes equal to the value of the signal S. Accordingly, the number of pulses counted during the time T required for V to become equal to S is a measurement of the value X of the physical magnitude detected, subject only to a coefficient of proportionality which is a function of the clock rate. This value can be displayed and/or can control an alarm signal which reacts when a predetermined threshold is passed at the remote location where the sensor conducting the measurement is positioned.

As will be further described below, the subject invention permits an alternating current signal on a two-wire transmission line to be utilized to supply power to at least one sensor associated with each such transmission line.

The device, according to the subject invention, includes a central data processing and control unit also referred to herein as a central station, at least one modulator-demodulator connected between the central station and a transformer located at one end of each transmission line (hereinafter referred to as an "upstream modem"); and at least one modulator-demodulator connected, preferably by a transformer, between the other end of the transmission line (hereinafter referred to as a "downstream modem") and each sensor.

The subject invention, in addition, may include at least one sensor which is powered from a source totally independent of each transmission line, such as an independently operated battery, a solar cell or generator.

A downstream modem may be connected to a downstream transformer of a two-wire transmission line either by means of a primary winding or by means of a secondary winding of the downstream transformer. When the downstream modem is connected by means of the primary winding, the modem may be connected to any point of the transmission line situated between the downstream transformer and the upstream transformer. In this case, the downstream transformer may be integrated with the sensor. When the downstream modem is connected by means of the secondary winding of the downstream transformer, the downstream transformer may be connected to any point in a line situated between the upstream transformer and the downstream modem. This second interconnection is diagrammatically shown in FIG. 2. More specifically, in FIG. 2 there is illustrated a central station represented by central processing unit 1, a plurality of upstream modems 2, a plurality of upstream transformers 3, a plurality of two-wire transmission lines 4, a plurality of downstream transformers 5, a plurality of downstream modems 6, and a plurality of sensors 7.

According to a particular embodiment, an isolation transformer may, in addition, be inserted if necessary at any point in at least one of transmission lines 4.

In a case where the device according to the present invention includes several transmission lines 4, the upstream transformers 3 have the function of providing voltage separation between transmission lines 4. In addition, each upstream transformer 3 provides voltage separation of each transmission line 4 from the upstream modem 2 to which it is connected.

Figure 3A:
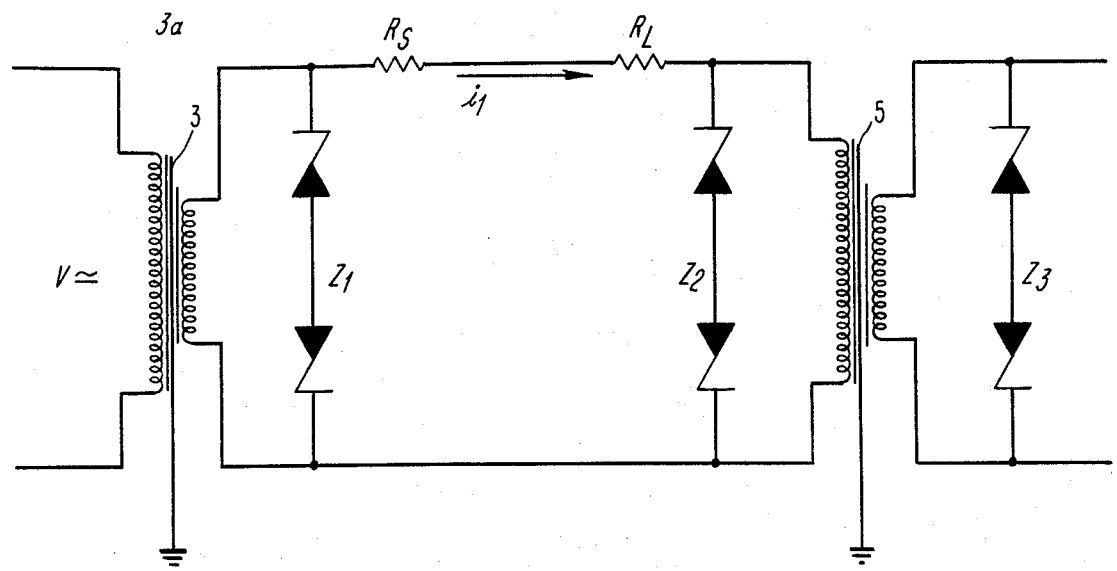
FIGS. 3a and 3b illustrate the connection of transformers to a transmission line in accordance with the teachings of the present invention.
Figure 3B:
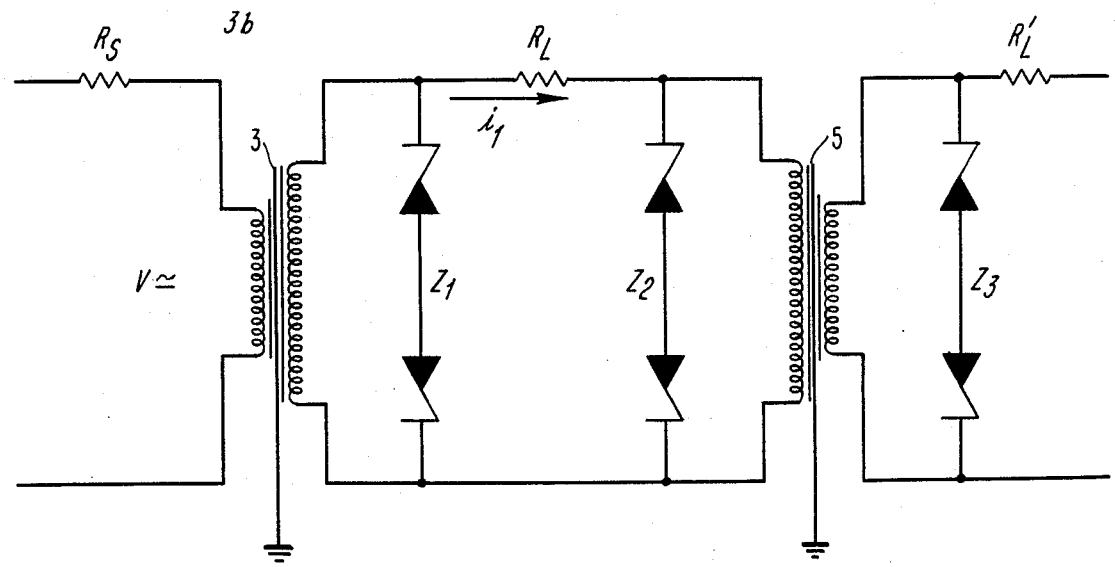

According to one embodiment, the upstream and downstream transformers 3, 5 are voltage step-down transformers. According to another embodiment, the upstream transformers 3 are voltage step-up transformers and the downstream transformers 5 are voltage step-down transformers. These two embodiments are illustratively shown in FIGS. 3a and 3b, respectively. In both embodiments, the intensity $i_1$ of current conveyed along the transmission lines is low with respect to the current which feeds the sensors at the downstream end of the line. Z1, Z2 and Z3 are zener diodes, $R_S$ is an additional resistance, and $R_L$ is the line resistance of transmission lines 4. V is the voltage available to upstream transformers 3. Knowing the voltage V, the length of transmission line 4 (and hence the value of line resistance RL), and the winding ratios of transformers 3 and 5, the value of RS may be readily determined by persons skilled in the art so as to provide a desired value of current $i_1$ passing along lines 4.

One or more (for example, from 1 to 8) upstream modems may be associated with one central station. One or more (for example 1 to 16) transmission lines may be associated with each upstream modem. Each transmission line is coupled to a downstream modem which can itself receive data from one or more sensors (for example from 1 to 8). Thus, a central station could process data coming from, for example, 1,024 sensors $(8 \times 16 \times 8)$.

Figure 2:
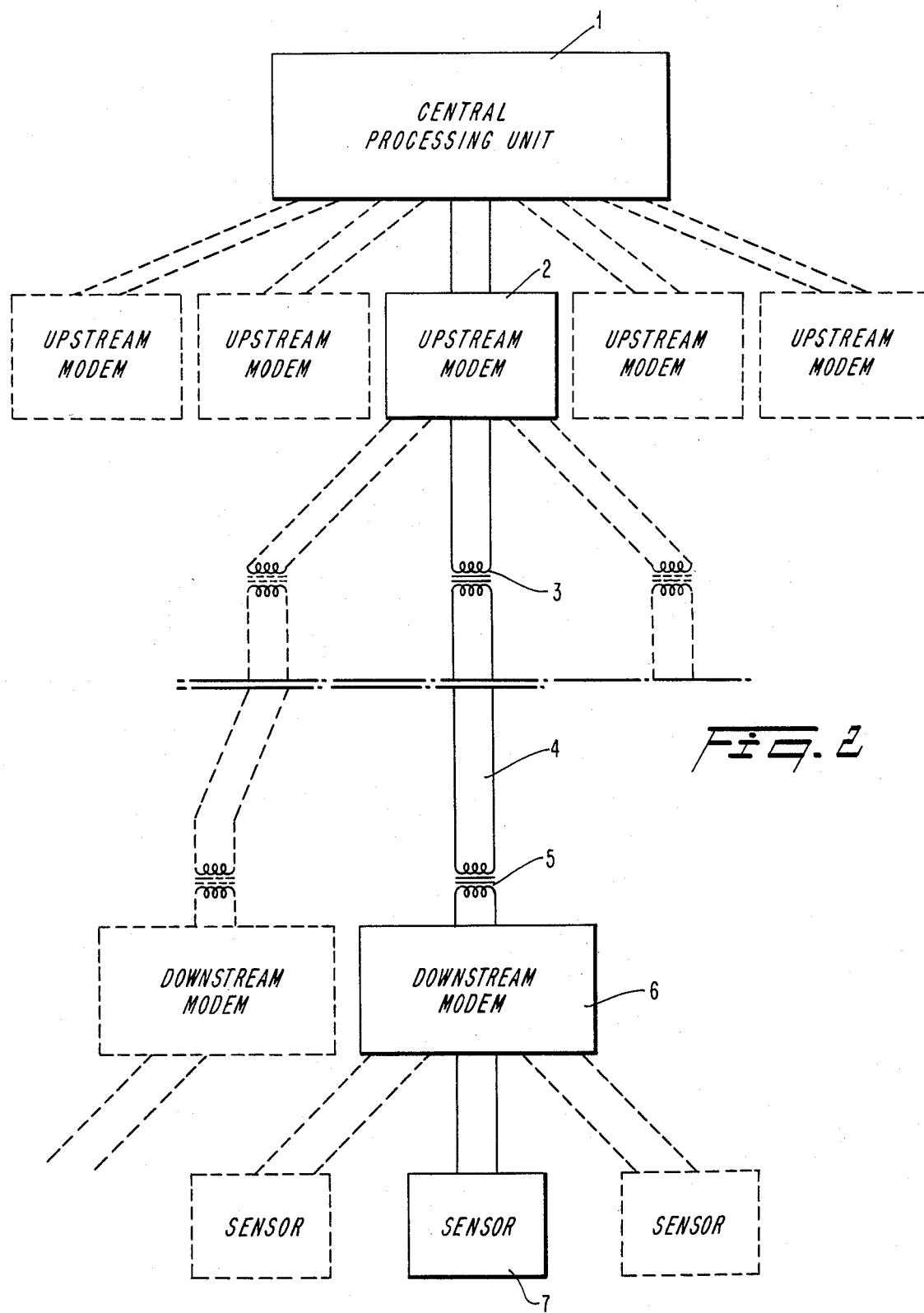
FIG. 2 diagrammatically illustrates the preferred embodiment of the present invention.

Sensor 7, as illustrated in FIG. 2, comprises a device which transforms a physical magnitude into an analog signal (voltage or current) and converts that analog signal into a digital signal. Sensor 7, therefore, comprises a detector and an analog-to-digital converter. At least one of the sensors 7 associated with each line 4 of FIG. 2 is powered by that line 4. The downstream modems 6 of FIG. 2 interrogate and receive data from sensors 7. Downstream modems 6 may have power supplies independent of transmission lines 4.

Upon interrogation by a downstream modem 6, the detector in the sensor 7 being interrogated provides an analog signal, most frequently a voltage, which is transformed by the analog-to-digital converter of sensor 7 into digital data. The link between any one of sensors 7 and a corresponding downstream modem 6 is either a conventional link, (a four-wire conducting line of which two wires are reserved for interrogation and two wires are reserved for transmission of data) or an opto-electric link which provides electrical isolation between sensors 7 and downstream modems 6. In this latter case, the opto-electrical device may be totally integrated either into a downstream modem 6 or into sensor 7. Such an opto-electronic device may, in the alternative, be divided between sensor 7 and downstream modem 6, with a transmitter and receiver being associated with the downstream modem 6 and a transmitter and receiver being associated with sensor 7. The link between sensor 7 and downstream modem 6 can be provided by means of optical fibers. The link between a sensor 7 and its downstream modem 6 may include, in addition, a two-wire line having the function of supplying sensor 7 with power.

The analog-to-digital conversion of signals emitted by the detectors of sensors 7 requires:

a. a circuit comprising an electronic clock and a pulse counter;

b. a circuit which is capable of generating $V = F(t)$ composed of n straight line segments and having the same characteristic form as the detector response curve $S = F(x)$ of the detector in sensor 7; and c. a comparator whose function is to continuously compare the value of the voltage $V = F(t)$ with the value of signal $S = F(x)$.

As long as V is less than S, the clock operates and causes the counter to advance. From the moment V equals S, the clock and the advancing of the counter both stop. The number of counts registered in the counter therefore represent a digital value proportional to the physical magnitude X to be measured, subject to a coefficient of proportionality which is a function of the clock rate.

A device capable of generating a function $V = F(t)$ composed of n straight line segments as shown in FIG.

5a may, for example, compose n+1 operational amplifiers. The comparator may be the (n+2)th operational amplifier.

Figure 4:
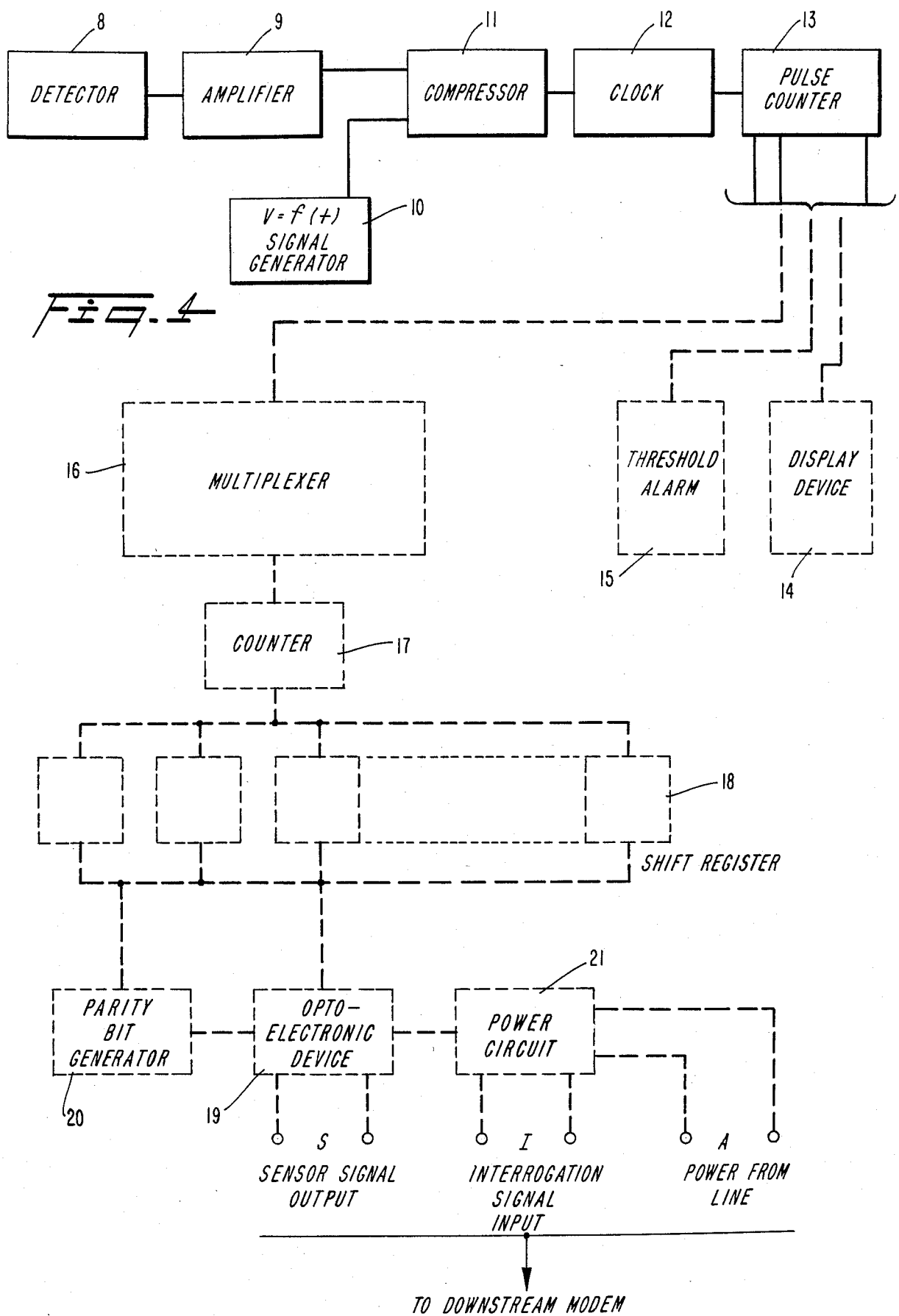
FIG. 4 is a schematic diagram of a sensor and related circuitry incorporating the teachings of the present invention.

FIG. 4 shows a sensor 7 in schematic form. In this figure there is shown a detector 8, amplifier 9, V=F(t) function generator 10, a comparator 11, a clock 12, and a pulse counter 13. The following elements may also be added to sensor 7: a display device 14, a device for triggering a threshold alarm 15, a multiplexer 16, a counter 17, a shift register 18, a device for providing a link between sensor 7 and downstream modem 6 illustrated as an opto-electronic device 19, an odd or even parity generator circuit 20, and a power circuit 21 for providing power to sensor 7 using the alternating current signal on the transmission lines of FIG. 2.

The sensor illustrated in FIG. 4, as employed in the process and device according to the subject invention, finds a particularly valuable application in the detection and/or measurement of the quantity of combustible gas in an atmosphere (for example, in an atmosphere within a mine), making it possible to monitor a multiplicity of work zones and thus to ensure the safety in those zones.

In this application, the sensor of FIG. 4 employs a filament detector which, during an interrogation sequence, is supplied with a given voltage. Current flowing through the filament of the detector heats the filament and, as a function of the quantity of combustible gas in the atmosphere surrounding the filament, raises the filament to a temperature which in turn modifies the resistance of the filament. This modification of resistance is detected, for example, by employing the filament as one arm of a Wheatstone bridge. The modification of resistance will be detected in the form of a voltage constituting a non-linear analog signal.

As the signal emitted by detector 8 of FIG. 4 is not linear, it is compared with a reference voltage V=F(t) supplied by signal generator 10. As mentioned before, signal generator 10 preferably comprises N+1 operational amplifiers. The output of signal generator 10 is coupled to one input of comparator 11 whereas the output of detector 8 is coupled through amplifier 9 to a second input of comparator 11. The output of comparator 11 is coupled to a clock 12 which in turn is coupled to a pulse generator 13. This circuit arrangement is illustrated in FIG. 5b, with the S and V signal inputs of comparator 11 clearly shown.

Figure 5A:
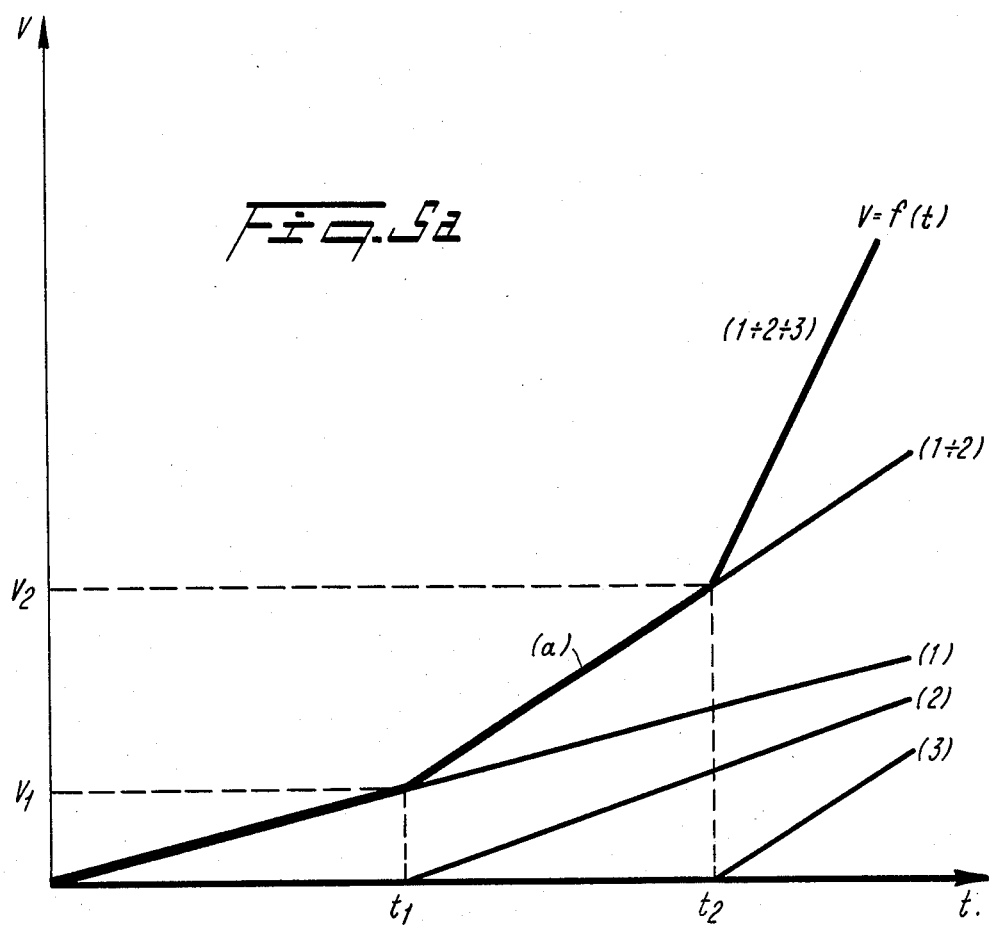
Figure 5B:
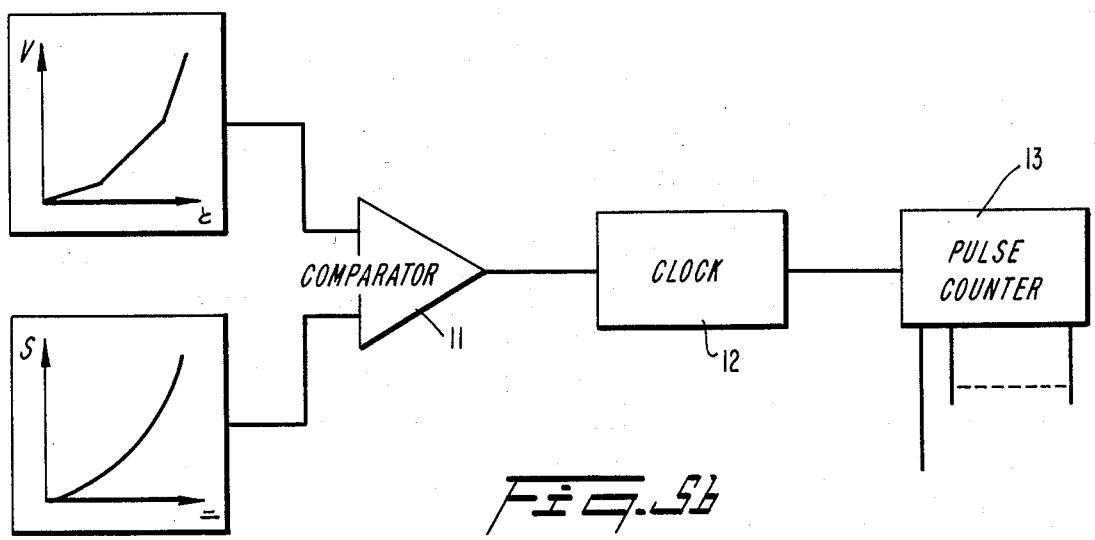

The circuit of FIG. 5b, accordingly, makes it possible to convert the parameter X into a digital value. More specifically, the parameter X is converted into a binary code and then is sent by means of downstream modem 7 of FIG. 2 over transmission line 4 to upstream modem 2 and finally to central processing unit 1. This digital value may be displayed at the location of sensor 7 and/or may also be used to feed a threshold alarm circuit 15 or display device 14 located in the physical proximity of detector 8.

In prior art systems which interrogate the output of a detector which is located in an atmosphere with a large quantity of combustible gas, (for example methane), it is normal that the interrogation process involve an inversion or reversal of polarity of the output signal from the detector. This prior art process is intended to maximize the certainty of the measurement obtained from the detector. However, use of such an inversion process does not provide a total guarantee that large quantities of combustible gas in the atmosphere will be accurately detected. Instead, it has been established that the technique of using signal inversion is not foolproof and that this technique, when employed with certain used detectors and even new detectors, can give rise to ambiguous indications of large quantities of combustible gas.

Nevertheless, it has been found possible to obtain a more unambiguous indication of whether the concentration of a quantity of combustible gas in an atmosphere is or is not greater than a predetermined threshold by interrogating a detector which has been consecutively supplied by two different values of power supply voltages. In a first step of such process, say from time 0 to time $T_1$ of an interrogation process, a detector may be supplied with a first voltage $V_1$. The output of such detector $S=F(x)$ is compared against a reference voltage $V=F(t)$ in comparator 13. If, from time 0 to time $T_1$ S is detected to be greater than V, first voltage $V_1$ is removed from the detector and the output of pulse counter 13 is used to indicate the quantity of combustible gas concentration detected. If S is not determined to be greater than V during the first stage from time 0 to time $T_1$, then a second stage is initiated in which the detector is supplied, from time $T_1$ to time $T_2$ with a second voltage $V_2$ higher than $V_1$. The maximum amplitude of the detector is measured at time $T_2$, if no S is not greater than V at some earlier point in time.

It will be possible to arrange a device according to the present invention, in the region of sensor 7 in such a way as to provide for a double power supply of the detector and to provide for the automatic cutting of its supply after the measurement sequences have been completed.

In addition to the sensor of FIG. 2, there is provided in accordance with the present invention, a downstream modem 6, an upstream modem 2, and a central processing unit 1. The downstream modem is preferably powered by a battery which is rechargeable through use of the alternating current signal supplied on transmission lines 4. Downstream modem 6 also includes an electronic clock whose pulses must be generated by the zero crossings of the alternating current signal conveyed by line 4. Downstream modem 6 further includes a remote control interrogation circuit required to recognize an interrogation message and, if such a message is recognized, to initiate operation of a bit counter and carry out an interrogation cycle through utilization of that bit counter. This interrogation cycle includes a sensor interrogation sequence, the reading of data on various sensors 7, and the sending of this data over lines 4 to upstream modems 2.

Upstream modems 2 comprise, if several lines 4 are coupled to them, two multiplexers which make it possible to couple upstream modems 2 to the line 4 having sensors to be interrogated. Upstream modems 2 also include a control circuit to ensure that the alternating current signal on a line 4 is cut or interrupted to form an interrogation request or to form the sending of an alarm signal. Upstream modems 2 further include a detection circuit to recognize that data is being received over lines 4 from downstream modem 6. Finally, upstream modems 2 require a circuit to integrate the central processing unit 1 which executes control of upstream modems 2 and data capture.

The function of central processing unit 1 is to control the operation of upstream modem 2, to capture and process data (in particular to trigger an alarm signal if necessary) and to manage the peripheral systems such as display screens, printers and the like.

Figure 6B:
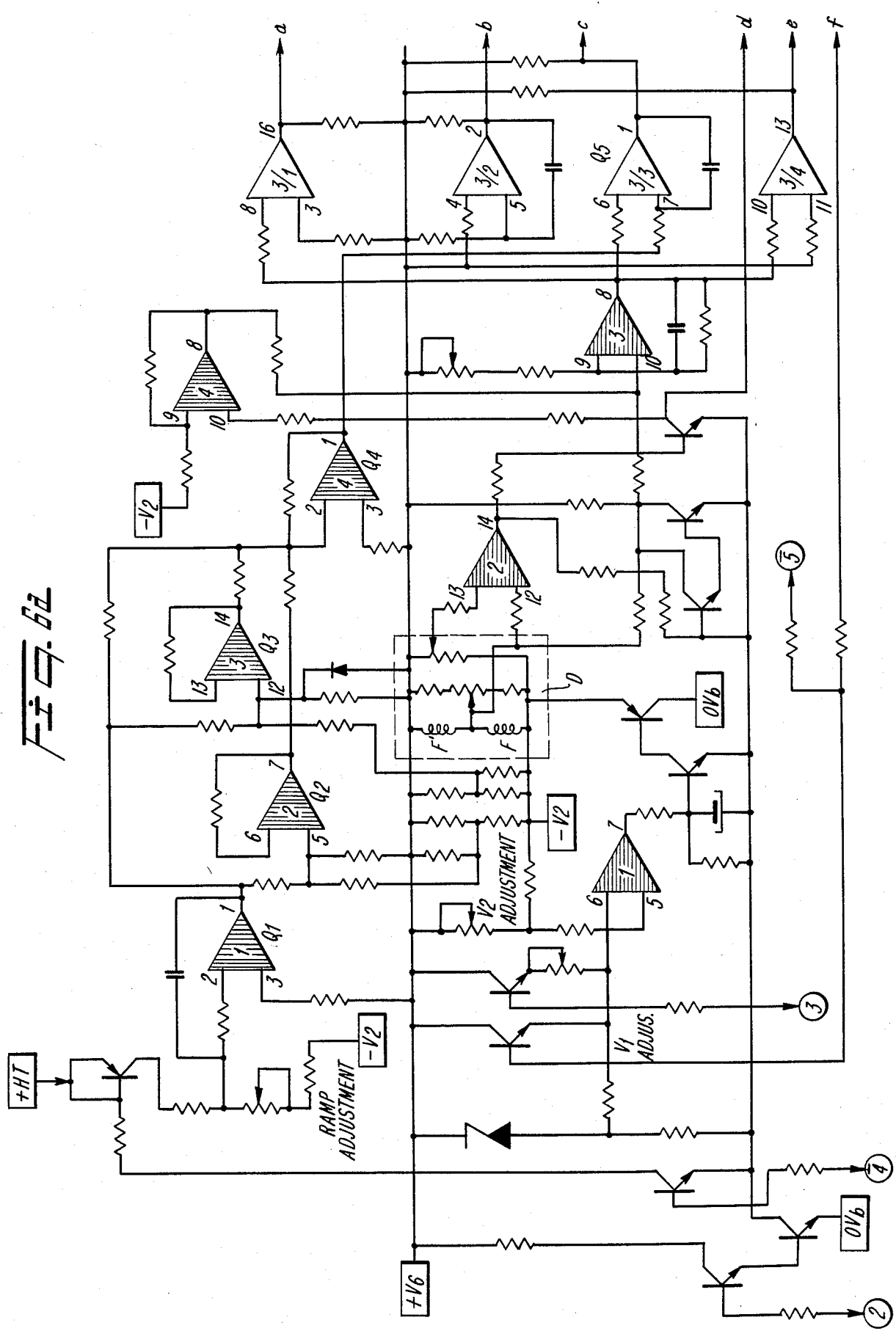
Figure 6B:
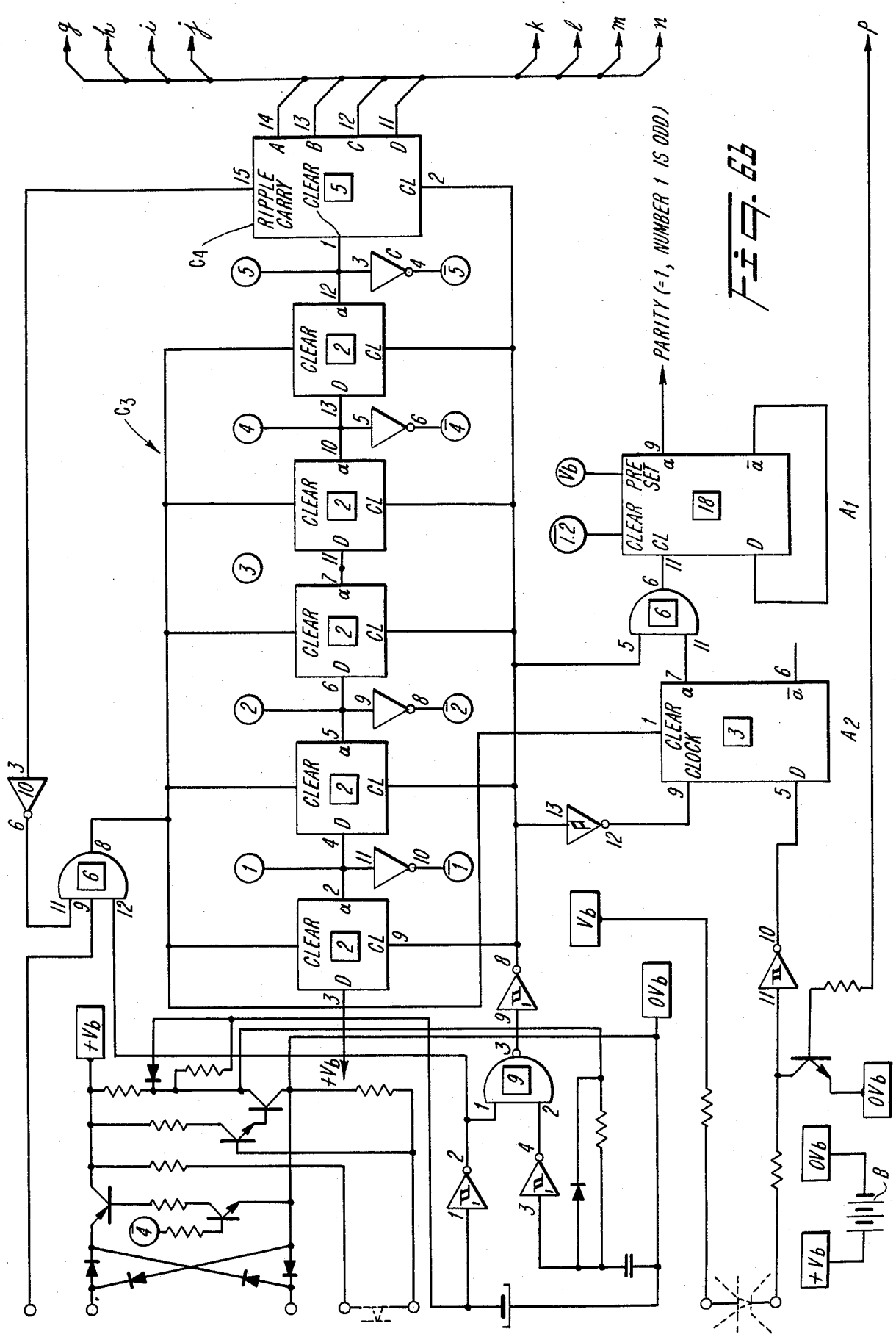

FIGS. 6a, 6b and 6c show a sensor arranged for measurement of a quantity of combustible gas in an atmosphere. Power is provided by a battery B which is rechargeable by the alternating current signal conveyed on the transmission line with which the sensor is associated. On these figures, the reference marks have the following significance:

D is a detector issuing a measurement signal voltage which is a function of the quantity of combustible gas. F is a filament of detector D. F' is a compensator filament of detector D. $Q_1$, $Q_2$, $Q_3$ and $Q_4$ are operational amplifiers which generate the function $V=F(t)$. $Q_5$ is an operational amplifier functioning as a comparator of $V=F(t)$ from operational amplifiers $Q_1$, $Q_2$, $Q_3$ and $Q_4$ and $S=F(x)$ which is the output of detector D. $A_1$ and $A_2$ are the circuits of a digital signal parity computer. $A_3$ is a bistable. $A_4$ is a clock divider circuit.

$B_1$ is a bistable. $B_2$ and $B_3$ are logic gates. $B_4$ and Z comprise an electronic clock. $B_5$ and $C_4$ are pulse counters. $B_6$ and $C_5$ are multiplexers. $C_1$ is a comparator. $C_3$ comprise a shift register.

The sensor of FIGS. 6a, b and c may also include indicators for displays and an alarm.

From $T=0$ corresponding to the sending of an interrogation signal to the sensor by interrupting two successive periods of the alternating current signal, the sensor of FIGS. 6a, 6b and 6c operates, for example, as follows: the downstream modem having recognized this interruption sends a series of pulses which control the shift register $C_3$ and the pulse counters $C_4$. At time $T=50$ ms, pulse number 1 enables output number 1. Enablement of output number 1 resets the bistables and indicators to 0. At time $T=70$ ms, pulse 2 enables output number 2. Enablement of output number 2 results in powering the analog circuits by the battery and powering of detector D with a voltage $V_1$. When a large quantity of combustible gas is present, a positive signal is then detected at comparator $Q_5$, and the powering of detector D is automatically terminated. At time $T=670$ ms, pulse number 3 enables output number 3. Enablement of output number 3 powers detector D with a second voltage $V_2$. Data gathered from the detector D is subsequently stored in bistable $B_1$. The output of bistable $B_1$ will serve in due course to send digital information in buffered form. At time $T=1970$ ms pulse number 4 enables output number 4. Enablement of output number 4 operates to disconnect recharging of the battery, trigger the analog-to-digital conversion, enable the detection of comparator $C_1$, and store the output of comparator $C_1$ in bistable $A_3$. At time $T=2040$ ms, pulse number 5 enables output number 5. Enablement of output number 5 terminates the detector power supply, ends the operation of counter $C_1$ and enables operation of multiplexers $C_5$, $B_6$ and counter $C_4$. Between time $T=2720$ and 4220 ms, pulse numbers 2 through 17 enable various output of multiplexers $C_5$, $B_6$ and counter $C_4$. Pulse number 18 at time $T=4360$ ms has no effect. Finally, pulse number 19 at time $T=4380$ ms has the effect of cutting the power supply to the sensor and putting the battery back on a charging mode of operation. A complete interrogation cycle thus lasts 4400 ms.

FIG. 7 illustrates a downstream modem. Power is supplied this downstream modem from a storage battery B which is recharged by the alternating current signal appearing on the transmission line 4. The circuit employed to selectively connect battery B for charging by the alternating current signal on lines 4 includes transistors $T_7$, $T_8$, and $T_9$ and diode $D_1$. The output of flip-flop 21-1 operates to control conduction of transistor $T_9$ which in turn controls conduction of transistor $T_7$ which still further controls conduction of transistors $T_8$. When transistor $T_8$ is conducting, diode $D_1$ and battery B are effectively connected in series across transmission line 4. However, upon operation of the interrogation sequence and subsequent sending of data over line 4, the conduction of transistor 8 is terminated, and battery B is effectively disconnected from any charging current supplied through diode $D_1$. During this disconnect condition, battery B nevertheless provides power for the modem disclosed in FIG. 7 and for the related sensor circuitry.

As described above, clock pulses must be generated when the alternating current signal passes through null. These pulses are generated by transistors $T_1$, $T_2$, $T_3$, $T_4$, $T_5$ and $T_6$ and by integrated circuits 24/1 and 24/2. When the value of the alternating current signal is less than 0.5 ma, there will be a null signal at the collector of transistor $T_6$ (node 2). When the line current exceeds $-7$ ma, there will be a positive signal at the collector of transistor $T_5$ (node 1). In that case node 1 commands "set" of a flip-flop circuit comprising integrating circuits 24/1 and 24/2. An output at node 2 commands "reset" for these flip-flops. Output node 3 represents the output of the flip-flops comprising integrated circuits 24/1 and 24/2. An output signal at node 3 operates as a clock pulse output which is delivered to a units counter CT.

The start of an interrogation sequence consists of detecting an interrupt of an alternating current signal for two consecutive periods. This interrupt is detected by a circuit comprising resistors $R_1$ and $R_2$, and capacitors $C_1$ and $C_2$. With $R_1$ equal to 150 k ohms, $R_2$ equal to 560 k ohms, and $C_1$ and $C_2$ both equal to $0.1\mu F$. The resultant circuit exhibits a time constant which can monitor an interruption which lasts between 12 and 180 ms. For an interruption which falls within this range, bit counter CT is initiated and the downstream modem begins its interrogation cycle. If the duration of interruption is less than 12 ms or in excess of 180 ms, for instance due to micro-interruptions of the current or an accidental line outage, bad contacts or the like, the downstream modem will not begin an interrogation cycle.

Data signal transmission by the downstream modem over line 4 takes place after automatically terminating the use of the alternating current signal over that line to provide power to the sensors and to the downstream modem, and after a 1500 ohm resistor $R_3$ has been connected to the line by means of electronic switches $T_{10}$ and $T_{11}$.

The 0 bit of FIG. 1 is obtained by closing the electronic switch $T_{13}$, $T_{14}$. The one bit of FIG. 1 is obtained by opening this same switch.

The message provided by the interrogated sensor thus is routed on the transmission line in the form that is schematically shown, for instance, by FIG. 1. This message is detected by the upstream modem. The detection circuit by the upstream modem is activated by a specific message from the downstream modem at the beginning of the data transmission sequence, for instance by transmission of a 0 bit followed by a 1 bit. The detection circuit measures the peak-to-peak voltage $2V_0$ shown on FIG. 1 to correspond to a 0 bit and then the peak-to-peak voltage $2V_1$ corresponding to a 1 bit. The detection circuit next determines the average value of these two voltages VM: $VM = [2V_0+2V_1]/2=V_0+V_1$. The resultant voltage VM will be stored. Detection will then be carried out by comparing the subsequent value V of the alternating current signal over the transmission line with the stored value VM. If the peak-to-peak value of the alternating current signal, 2V exceeds VM, then a 1 bit is determined to have been received. If the peak-to-peak value of the input signal, 2V, is less than VM, then a 0 bit is determined to have been received.

In operation of the downstream modem illustrated in FIG. 7, a time base is established which comprises a sequence divided into 17 time units. Each time unit lasts for 13 complete cycles of the alternating current signal, i.e., 26 half cycles. The first 8 time units are used in the interrogation of sensors. A base counter CT having individual units and tens sections counts the number of times the alternating current signal passes through null. For every 26 times a passage through null is detected, this base counter adds 1 to a unit counter UT having outputs 1–17. Each data bit from the downstream modem will be introduced over the transmission line in accordance with the status of the base counter CT and the unit counter UT. For instance, a first data bit SM is moved into the 20–21 position of base counter CT and into the position 8 of counter UT.

A set of logic circuits LC (shown by shading in FIG. 7) operates in conjunction with a related counter to generate a sensor interrogation sequence. Flip-flops FF of FIG. 7 permit a sufficiently long period of time to pass between the time when the downstream modem asks a sensor to send a data bit and the time when the modem actually transmits that bit over the line.

The flip-flop 21-1 stores the line interrupt and initiation sequence while flip-flop 22-2 stores a remote alarm signal if such a signal is sent by the central processing unit, provided such signal is sent at the 17th time unit. Flip-flop 21-1 has the task at the time the message is transmitted over the transmission line to disconnect the storage battery and to connect the 1500 ohm resistor R₃.

Synchronization is maintained between an upstream modem and downstream modem by maintaining the phase of the alternating current signal constant throughout the system. The phase between the primary and secondary currents of the line transformers is kept constant by feeding this current through a high value resistor to the primary transformer. The alternating current signal in the line is thereby maintained constant as long as the downstream modem is connected and properly operating for a line length less than 10 kilometers.

Additional advantages and modifications will readily occur to those skilled in the art. The invention in its broader aspects is, therefore, not limited to the specific details representative of apparatus and illustrative of examples shown and described. Accordingly, departures may be made from such details without departing from the spirit or scope of applicants' general inventive concept.

We claim for Letters Patent:

1. A process for remotely transmitting data signals issued by at least one sensor from that sensor to a central station over a transmission line comprising the steps of:
    (a) supplying to said transmission line an alternating current signal of approximately constant current intensity;
    (b) coupling said sensor to said line to power said sensor using said alternating current signal on said line;
    (c) employing said alternating current signal to transmit an interrogation signal from said central station to said sensor over said transmission line; and
    (d) employing said alternating current signal to transmit a multibit, digital data signal from said sensor to said central station over said transmission line is response to receipt of said interrogation signal by transmitting over said line a complete bit of digital information in a cycle of said alternating current signal by changing, over a complete cycle, the value of a load applied at said sensor to said transmission line at zero-cross over points of said alternating current signal.

2. The process according to claim 1 including the step of maintaining said alternating current signal in a constant phase relationship throughout said line.

3. The process according to claim 1 including the further step of using said alternating current signal to power electronic circuits associated with said sensor.

4. The process according to claim 1, 2 or 3 including the step of employing said alternating current signal to transmit an interrogation signal over said transmission line from said central station to a sensor which is not powered by said alternating current signal.

5. The process according to claim 1 wherein said step of transmitting an interrogation signal includes removing said alternating current signal from said transmission line during two consecutive cycles of said alternating current signal.

6. A process according to claim 1 further comprising the steps of generating a non-linear analog output signal responsive to operation of said at least one sensor; and converting said non-linear analog signal into a digital signal by comparing said non-linear analog signal to a reference voltage which is a function of time and whose representative curve comprises n straight line segments.

7. A process of claim 1 or 2 further including the step of detecting and/or measuring a quantity of combustible gas in an atmosphere using at least one of said sensors.

8. A process of claim 6 further including the step of detecting and/or measuring a quantity of combustible gas in an atmosphere using at least one of said sensors.

9. A device for remotely transmitting data signals issued by at least one sensor from that sensor to a central station comprising:
    (a) at least one transmission line;
    (b) means for supplying an alternating current signal to said transmission line;
    (c) a first transformer coupling a first end of said transmission line to said central station;
    (d) a second transformer coupling a second end of said transmission line to said sensor;
    (e) means for employing said alternating current signal to transmit an interrogation signal from said central station to said sensor over said transmission line; and
    (f) means for employing said alternating current signal to transmit a multibit, digital data signal from said sensor to said central station over said transmission line in response to said interrogation signal by transmitting over said line a complete bit of digital information in a cycle of said alternating current signal by changing, over a complete cycle, the value of a load applied at said sensor to said transmission line at zero-crossover points of said alternating current signal.

10. A device according to claim 9 for remotely transmitting data signals issued by a plurality of sensors from those sensors to a central station further including means for powering at least one of said sensors using said alternating current signal on said transmission line.

11. A device according to claim 10 further including:
(a) at least one modulator-demodulator connected between said central station and said first transformer; and
(b) at least one second modulator-demodulator connected between said second transformer and at least one of said sensors.

12. A device according to claim 9, 10 or 11 for remotely transmitting data signals issued by a plurality of sensors from those sensors to a central station including means for powering at least one of said sensors by a source which is independent of said alternating current signal.

13. A device according to claim 11 wherein the primary winding of said secondary transformer is connected to said second modulator-demodulator.

14. A device according to claim 11 wherein the secondary of said secondary transformer is connected to said second modulator-demodulator.

15. A device according to claim 9, 10, 11, 13 or 14 further including an isolating transformer interposed at a point on at least one of said transmission lines.

16. A device according to claim 11, 13 or 14 for remotely transmitting data signals issued by a plurality of sensors from those sensors to a central station further including an opto-electronic device for coupling at least one of said sensors to said second modulator-demodulator.

17. A device for remotely transmitting data signals issued by at leasst one sensor from that sensor to a central station comprising:
(a) at least one transmission line;
(b) means for supplying an alternating current signal to said line;
(c) a first transformer coupling a first end of said transmission line to said central station;
(d) a second transformer coupling a second end of said transmission line to said sensor;
(e) first means for transmitting an interrogation signal from said central station to said sensor over said transmission line by removing said alternating current signal from said line for a predetermined period of time; and
(f) second means for transmitting a data signal from said sensor to said central station over said transmission line in response to said interrogation signal comprising means for selectively presenting a first value of resistance across said line to represent a 0 bit data signal and for presenting a second different value of resistance across said line to represent a 1 bit data signal and for changing back and forth between said first and second values during zero-crossover of said alternating current signal.

18. A device of claim 17 wherein said second means comprises:
(a) a storage battery recharged by said alternating current signal appearing on said transmission line;
(b) a clock circuit generating a pulse when said alternating current signal passes through null;
(c) a unit counter;
(d) a base counter having an input coupled to receive said pulses from said clock circuit and having an output coupled as an input to said unit counter;
(e) a set of logic circuits for interrogating said sensor to obtain said data signal in the form of a plurality of data bits in response to operation of said sensor and in response to operation of said base counter;
(f) first and second flip-flops connected to said set of logic circuits to control the time period between the sending of said data bits by said sensor and the transmission of those bits over said line;
(g) means, including a third flip-flop and a resistor for disconnecting said storage battery and connecting said resistor between two wires of said transmission line in response to receipt of said interrogation signal; and
(h) an electronic switch coupled in parallel to said resistor and having a control electrode coupled to the output of said first and second flip-flops to close said switch in response to receipt of said data bits from said first and second flip-flops, thereby transmitting said data over said transmission line.

* * * * *